(12) United States Patent
    Vayser (10) Patent No.: US 11,903,567 B2
(45) Date of Patent: Feb. 20, 2024

(54) BODY CAVITY ILLUMINATION SYSTEM

(71) Applicant: Invuity, Inc., San Francisco, CA (US)

(72) Inventor: Alex Vayser, Mission Viejo, CA (US)

(73) Assignee: Invuity, Inc., San Francisco, CA (US)

( * ) Notice: Subject to any disclaimer, the term of this patent is extended or adjusted under 35 U.S.C. 154(b) by 495 days.

(21) Appl. No.: 17/148,502

(22) Filed: Jan. 13, 2021

(65) Prior Publication Data
US 2021/0127961 A1    May 6, 2021

Related U.S. Application Data

(63) Continuation of application No. 15/497,132, filed on Apr. 25, 2017, now Pat. No. 10,912,453, which is a
(Continued)

(51) Int. Cl.
*A61B 1/07*    (2006.01)
*A61B 1/06*    (2006.01)
(Continued)

(52) U.S. Cl.
CPC .............. *A61B 1/07* (2013.01); *A61B 1/0011* (2013.01); *A61B 1/00066* (2013.01);
(Continued)

(58) Field of Classification Search
CPC ...... F21V 33/0068; F21V 5/008; F21V 5/006; F21V 5/02; F21V 15/01; F21V 9/00;
(Continued)

(56) References Cited

U.S. PATENT DOCUMENTS 1,351,562 A * 8/1920 Foster .................. G02B 6/0006
                                                    600/176
2,480,178 A * 8/1949 Zinberg ............... G02B 6/0005
                                                    362/621
(Continued)

FOREIGN PATENT DOCUMENTS

EP        0101781 A1    3/1984
GB        2078526 A     1/1982

OTHER PUBLICATIONS

Notice of Allowance dated Nov. 7, 2013 for U.S. Appl. No. 11/432,898.
(Continued)

*Primary Examiner* — David W Bates
(74) *Attorney, Agent, or Firm* — McDonnell Boehnen Hulbert & Berghoff LLP (57) ABSTRACT

A cavity illumination system according to the present disclosure may include one or more illumination elements composed of a transparent or semi-transparent, biocompatible sterilizable polymer and one or more illumination sources. The sterilizable polymer operates as a waveguide. An illumination element may incorporate micro structured optical components such as for example gratings, prisms and or diffusers to operate as precision optics for customized delivery of the light energy. The micro structured optical components may also be used to polarize and/or filter the light energy entering or exiting the illumination element.

13 Claims, 9 Drawing Sheets

Related U.S. Application Data continuation of application No. 14/175,875, filed on Feb. 7, 2014, now abandoned, which is a continuation of application No. 11/432,898, filed on May 12, 2006, now Pat. No. 8,684,577.

(60) Provisional application No. 60/681,074, filed on May 13, 2005, provisional application No. 60/681,119, filed on May 13, 2005, provisional application No. 60/681,089, filed on May 13, 2005.

(51) Int. Cl.
| | |
|---|---|
| *A61B 1/247* | (2006.01) |
| *A61B 1/32* | (2006.01) |
| *F21V 8/00* | (2006.01) |
| *F21V 33/00* | (2006.01) |
| *A61B 17/02* | (2006.01) |
| *A61B 1/267* | (2006.01) |
| *A61B 1/00* | (2006.01) |
| *A61B 1/303* | (2006.01) |

(52) U.S. Cl.
CPC .......... *A61B 1/0623* (2013.01); *A61B 1/0676* (2013.01); *A61B 1/0684* (2013.01); *A61B 1/247* (2013.01); *A61B 1/267* (2013.01); *A61B 1/303* (2013.01); *A61B 1/32* (2013.01); *A61B 17/02* (2013.01); *F21V 33/0068* (2013.01); *G02B 6/0048* (2013.01)

(58) Field of Classification Search
CPC ........ A61B 1/32; G02B 6/001; G02B 6/0036; G02V 6/0048
See application file for complete search history.

(56) References Cited

U.S. PATENT DOCUMENTS

| | | | |
|---|---|---|---|
| 3,638,644 A | 2/1972 | Reick | |
| 3,641,332 A | 2/1972 | Reick et al. | |
| 3,752,561 A * | 8/1973 | Klemt | G02B 6/0006 385/146 |
| 3,890,960 A | 6/1975 | Wunsch et al. | |
| 4,012,630 A * | 3/1977 | Gareis | F21V 13/04 362/582 |
| 4,226,228 A | 10/1980 | Shin et al. | |
| 4,562,832 A | 1/1986 | Wilder et al. | |
| 4,592,344 A | 6/1986 | Scheer | |
| 4,597,030 A | 6/1986 | Brody et al. | |
| 4,605,990 A | 8/1986 | Wilder et al. | |
| 4,643,172 A | 2/1987 | Taff et al. | |
| 4,697,578 A | 10/1987 | Burgin | |
| 4,807,599 A | 2/1989 | Robinson et al. | |
| 4,842,356 A | 6/1989 | Mori | |
| 4,961,617 A | 10/1990 | Shahidi et al. | |
| 5,020,933 A | 6/1991 | Salvestro et al. | |
| 5,035,232 A | 7/1991 | Lutze et al. | |
| 5,179,938 A | 1/1993 | Lonky | |
| 5,353,786 A | 10/1994 | Wilk | |
| 5,588,836 A | 12/1996 | Landis et al. | |
| 5,622,423 A * | 4/1997 | Lee | F21L 4/02 362/186 |
| 5,719,938 A | 2/1998 | Haas et al. | |
| 5,785,648 A | 7/1998 | Min | |
| 5,873,818 A | 2/1999 | Rothfels | |
| 5,914,760 A * | 6/1999 | Daiku | G02B 6/0053 349/95 |
| 6,053,623 A * | 4/2000 | Jones | F21V 7/28 362/348 |
| 6,147,725 A | 11/2000 | Yuuki et al. | |
| 6,185,356 B1 | 2/2001 | Parker et al. | |
| 6,217,514 B1 | 4/2001 | Gruen et al. | |
| 6,428,473 B1 | 8/2002 | Leonard et al. | |
| 6,504,985 B2 | 1/2003 | Parker et al. | |
| 6,514,077 B1 | 2/2003 | Wilk | |
| 6,814,699 B2 | 11/2004 | Ross et al. | |
| 6,857,771 B2 * | 2/2005 | Guerrieri | G02B 6/001 362/186 |
| 6,964,570 B2 | 11/2005 | Ghim | |
| 6,974,321 B2 | 12/2005 | Hirsch et al. | |
| 7,021,807 B2 | 4/2006 | Chew | |
| 7,188,984 B2 * | 3/2007 | Sayers | F21S 41/28 362/240 |
| 7,238,184 B2 | 7/2007 | Megerman et al. | |
| 7,306,559 B2 | 12/2007 | Williams | |
| 7,871,375 B2 | 1/2011 | Talieh | |
| 8,360,596 B2 * | 1/2013 | Bertken | F21L 4/027 362/120 |
| D682,724 S * | 5/2013 | Campman | D10/114.9 |
| 8,628,209 B2 | 1/2014 | Shew | |
| 8,684,577 B2 | 4/2014 | Vayser | |
| 8,956,038 B2 * | 2/2015 | Kusuura | G02B 6/0048 362/616 |
| 9,678,267 B2 * | 6/2017 | Robinson | H04N 13/368 |
| 2001/0015893 A1* | 8/2001 | Campman | F21V 31/00 362/184 |
| 2002/0001202 A1 | 1/2002 | Williams et al. | |
| 2002/0058931 A1* | 5/2002 | Parker | G02B 6/001 606/16 |
| 2005/0073473 A1 | 4/2005 | Carpinelli et al. | |
| 2006/0256575 A1 | 11/2006 | Vayser | |
| 2010/0041955 A1* | 2/2010 | Grey | A61L 29/041 600/212 |
| 2012/0041268 A1* | 2/2012 | Grey | A61B 1/267 600/199 |
| 2014/0153278 A1 | 6/2014 | Vayser | |
| 2016/0015467 A1* | 1/2016 | Vayser | G02B 1/048 600/245 |

OTHER PUBLICATIONS

Office action dated Feb. 3, 2012 for U.S. Appl. No. 11/432,898.
Office action dated Feb. 9, 2017 for U.S. Appl. No. 14/175,875.
Office action dated Mar. 16, 2016 for U.S. Appl. No. 14/175,875.
Office action dated Apr. 28, 2011 for U.S. Appl. No. 11/432,898.
Office action dated May 8, 2014 for U.S. Appl. No. 14/175,875.
Office action dated May 10, 2013 for U.S. Appl. No. 11/432,898.
Office action dated May 19, 2015 for U.S. Appl. No. 14/175,875.
Office action dated May 25, 2010 for U.S. Appl. No. 11/432,898.
Office action dated Jun. 3, 2009 for U.S. Appl. No. 11/432,898.
Office action dated Aug. 25, 2008 for U.S. Appl. No. 11/432,898.
Office action dated Sep. 6, 2007 for U.S. Appl. No. 11/432,898.
Office action dated Sep. 28, 2011 for U.S. Appl. No. 11/432,898.
Office action dated Oct. 14, 2010 for U.S. Appl. No. 11/432,898.
Office action dated Dec. 4, 2014 for U.S. Appl. No. 14/175,875.

* cited by examiner

BODY CAVITY ILLUMINATION SYSTEM

CROSS-REFERENCES TO RELATED APPLICATIONS

The present application is a continuation of U.S. patent application Ser. No. 15/497,132, filed Apr. 25, 2017, which is a continuation of U.S. patent application Ser. No. 14/175,875, filed Feb. 7, 2014, which is a continuation of U.S. patent application Ser. No. 11/432,898, filed May 12, 2006, which claims priority from U.S. Provisional Patent Application No. 60/681,074, filed May 13, 2005, U.S. Provisional Patent Application No. 60/681,119, filed May 13, 2005, and U.S. Provisional Patent Application No. 60/681,089, filed May 13, 2005, the full disclosures of which are incorporated herein by reference.

BACKGROUND OF THE INVENTION

1. Field of the Invention

The inventions described below relate to the field of medicine and more specifically, to providing body cavity illumination for use by doctors and dentists during medical and dental procedures.

2. Background of the Invention

Various illuminating means have been employed in the past to illuminate natural cavities within the human body in order to facilitate examination and performance of medical procedures by medical professionals. Illumination devices currently on the market employ projected, directional light. Some devices such as commercially available specula have their lighting means disposed on the lower blades of the specula where a heavy discharge, e.g., a vaginal discharge, can pool and obscure the light source. Other devices employ projected directional light, however, these illumination means merely provide illumination in a capacity limited to the area directly in front of the device or the optical fiber. These drawbacks make it difficult for medical personnel to perform examinations or procedures because their ability to see is diminished due to poor illumination.

Conventional methods of illumination in dentistry primarily consist of the use of overhead lighting or the use of head mounted lighting by dental professionals. Although these methods have been used for many years, they have many drawbacks. During dental examinations and procedures, dentists are often positioned between the light source and the patient's mouth, which blocks the light and creates shadows in the patient's mouth making it difficult to see.

It is frequently necessary in medical procedures to insert an endotracheal tube into the trachea of a patient for the purpose of performing diagnostic tests or for the introduction of some means of ventilation, oxygenation, and/or airway protection. Even in the best situations, intubation is often difficult and can give rise to complications. In many patients, establishment of the airway is particularly difficult due to morphologic anomalies such as a large tongue, excessive pharyngeal or laryngeal soft tissue, or tracheal displacement, as well as physiologic events such as laryngospasm, regurgitation of gastric materials, bleeding, or foreign bodies aspiration. These morphologic anomalies and/or events make it difficult to visualize the posterior pharyngeal area and larynx with conventional laryngoscopic maneuvers. In emergency situations, attempts to intubate such patients are difficult and time consuming. Inability to expeditiously intubate the patient and protect the airway can lead to significant hypoxemia, myocardial ischemia, and brain injury. Cases of death have also been related to complications caused by the inability to quickly and clearly see the larynx and trachea. Proper illumination is critical to safely and quickly insert an endotracheal tube into a patient.

Conventional laryngoscopes are often only able to provide illumination to the area directly in front of the blade or the optical fiber. These drawbacks make it difficult for medical personnel to perform intubations because their ability to see is diminished due to poor field of illumination.

Anoscopes are used to view the anal cavity and lower rectum. Illumination is provided with a fiber optic light pipe that provides only a spot of light that must be moved around to view the cavity. Some anoscopes are provided with fiber optic fibers arranged in a ring around the tip of the device. Such devices are very expensive to manufacture and only provide a ring of light due to the small divergence angle of the fiber optic light output, thereby poorly illuminating the cavity walls.

An inefficient waveguide in conventional devices may experience significant light loss; typically 60% of light may be lost from input to output. Such a light guide would require a high power LED to provide sufficient light. A high power LED requires a lot of power and generates significant heat, thereby requiring large batteries and bulky and inconvenient heat sinking devices and methods that add to the size and increase the difficulty of using such a device. Other high power light sources often require noisy fans, which may disturb the medical personnel conducting a surgery or medical exam.

What is needed is a more effective, simple and inexpensive means of illuminating body cavities.

BRIEF SUMMARY OF THE INVENTION

A cavity illumination system according to the present disclosure may comprise one or more illumination elements composed of a transparent or semi-transparent, biocompatible sterilizable polymer and one or more illumination sources. The sterilizable polymer operates as a waveguide. An illumination element may incorporate micro structured optical components such as for example gratings, prisms and or diffusers to operate as precision optics for customized delivery of the light energy. The micro structured optical components may also be used to polarize and/or filter the light energy entering or exiting the illumination element.

For example, a dental retractor may have a substantially U-shaped waveguide to confine and guide a propagating electromagnetic wave. When in use, the light source in the dental retractor provides an electromagnetic wave, which is confined and guided by the polymer resulting in the illumination of the oral cavity.

Alternatively, an external reusable light source may be attached to the disposable dental retractor to provide a source of light, said light being guided by the waveguide to optical structures specifically designed to illuminate particular areas of the oral cavity. Other similar dental devices may be so configured to provide illumination of the oral cavity, for example, cheek retractors, cheek expanders, combination lip and cheek retractors, tongue shields, bite blocks, intraoral mirrors used in photography, and the like.

In an alternate example, an illuminated laryngoscope may include a disposable blade comprising a biocompatible sterilizable polymer. When in use, the light source in the blade, or in optical communication with the blade provides an electromagnetic wave, which is confined and guided by the polymer resulting in the illumination of the trachea of the patient.

In modern practice, a non-disposable metal blade is often preferred due to the forces applied during use. In an alternate configuration, a disposable waveguide may be attached to the metal blade or inserted into a groove in the metal blade. When in use, the light source in the waveguide, or in optical communication with the waveguide provides light that is confined and guided in the waveguide until it reaches optical structures for directing the outgoing light to selected areas to be illuminated.

In another example, a speculum illumination system may comprise a gynecological speculum having detachable blades comprising a biocompatible sterilizable polymer. The illumination source is in optical communication with the blades the sterilizable polymer functions as a waveguide.

A body cavity illumination system waveguide is designed and fabricated to optimize light transfer from the light source or fiber optic input cable and minimize light loss from the waveguide in order to provide an efficient light transmission system. Efficiency is particularly important for LED and other light sources, e.g., tungsten or xenon lamps, because it directly determines the required brightness of the LED. An efficient waveguide, one in which light loss is typically less than 30%, allows a much lower power LED or other light source to be used, thereby significantly reducing or eliminating the need for special heat sinking devices and methods and improving the usability of the device. The design of an efficient body cavity illumination waveguide may involve special design of the light input portion of the waveguide to efficiently capture the incoming light, design and fabrication of the light reflecting walls of the waveguide to maintain surface finish to maximize reflection and reduce light lost through refraction, the use of reflective or dampening coatings, the design of light directing optical structures that direct the light toward the light output optical structures while minimizing light loss through refraction, and/or the design of light output optical structures that maximize light exiting the waveguide through refraction, particularly refraction of light in certain directions, while minimizing light lost through reflection.

DETAILED DESCRIPTION OF THE INVENTION

Figures 1, 2:
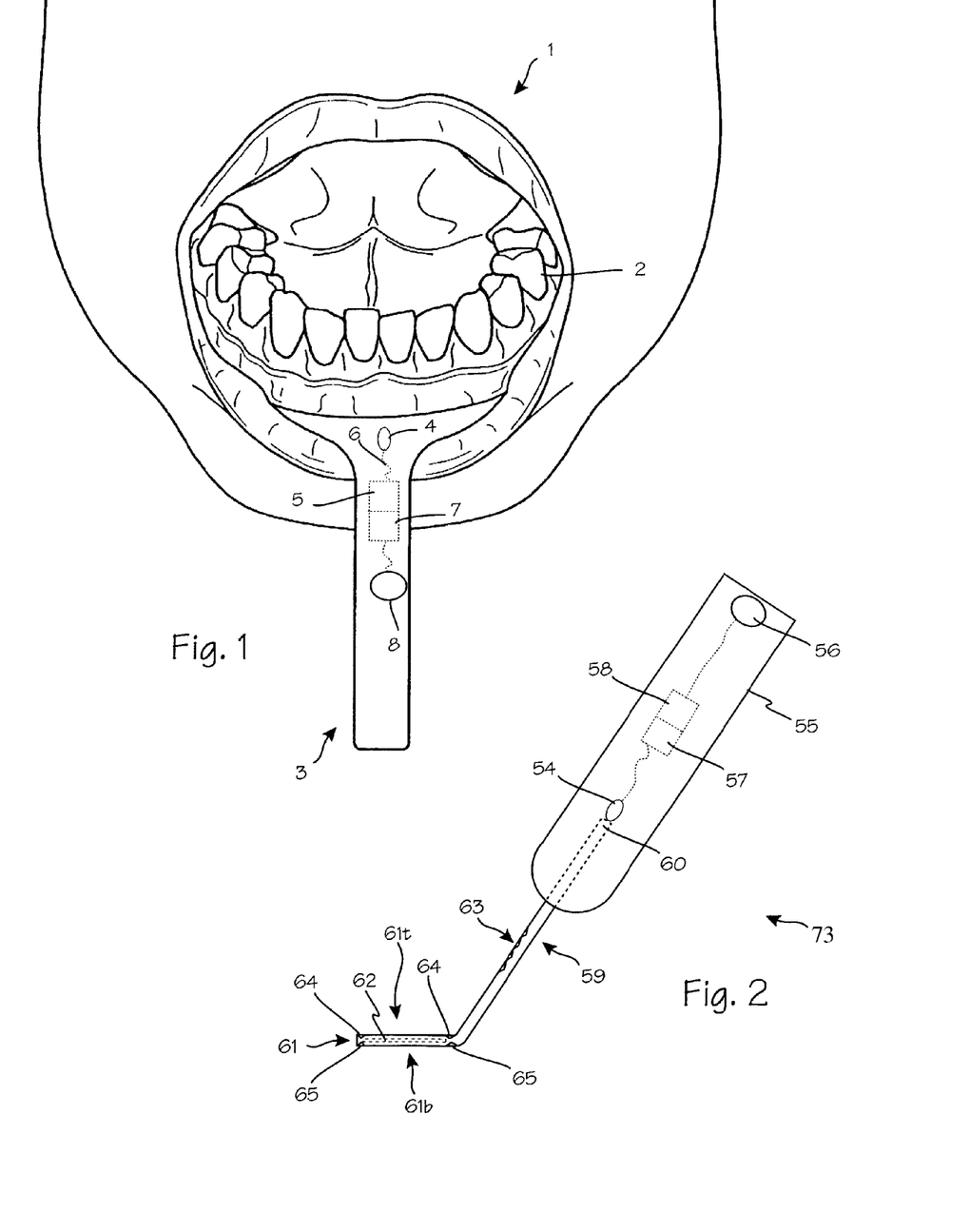
FIG. 1 is a front view of a patient's oral cavity during a dental examination using a cavity illumination system according to the present disclosure.
FIG. 2 is a side view of an alternate cavity illumination configuration.

FIG. 1 illustrates a patient's oral cavity 1 during a dental examination. The patient's mouth is opened with a cheek or dental retractor, exposing the patient's teeth 2. The dental retractor comprises biocompatible sterilizable polymer that acts as a waveguide and further comprises an illumination source 3. The illumination source comprises an LED (light emitting diode) 4, battery 5, a conductor 6 electrically connecting the battery and the LED, and an LED control circuit 7 and switch 8. The switch may have pressure sensor causing a connection between the battery and the LED when the patient's lips or cheeks press against the retractor and resulting in illumination. The LED is preferably a white-light LED, which provides a bright, white light. The battery may be provided in any form, but is preferably a lithium ion polymer battery provided in small, conformal case. The control circuit, including a switch, is provided in the case or any convenient location.

Dental illumination system 73 of FIG. 2 is integrated into a dental mirror. An illumination source is integrated into handle 55. The illumination source includes switch 56, battery 57, any suitable switching and drive circuit such as circuit 58 and a suitable light element such as LED 54, preferably a bright white LED. The battery may be of any suitable type, preferably a lithium ion polymer battery. Light is conducted into the cavity using waveguide 59 with an input portion 60 positioned next to the LED to capture the light emitted from the LED. The waveguide exits the handle and forms a frame 61 for mirror 62.

Alternatively, top face 61t of the waveguide may be coated with a mirror finish to implement the mirror. Output optical structures such as structures 63 may be located where the waveguide exits the handle portion to shine light into the mirror that is then reflected to the anatomical structures to be viewed. Alternatively, output optical structures such as structures 64 may be situated on top waveguide surface 61t along the periphery of the mirror. Light emanating from these structures is directed upwards to illuminate the anatomical structures viewed in the mirror. These structures may be specially designed to reduce the light directed toward the user and/or maximize the light directed toward the anatomical structures to be viewed.

The bottom side of the waveguide frame, surface 61b, may also contain output optical structures such as structures 65 to illuminate anatomical structures when the mirror is reversed and used as a retractor. Output optical structures 65 on the bottom surface of the waveguide frame may be placed along the periphery, along a portion of the waveguide frame face, and/or across the entire area of the bottom surface. The waveguide frame may also include light directing structures to direct light from the input portion to the output portion of the waveguide frame. Light output structures may be combined, such as structures 63 for use with the mirror and structures 65 for use as a retractor, or structures 64 for use with the mirror and structures 65 for use as a retractor. Waveguide frame 59 is designed to maximize light transmission efficiency to enable use of a lower power LED, thereby allowing a smaller heat sink and smaller batteries that then allow the handle to be smaller in size and easier to manipulate by a user.

Waveguide 59 may also be modified to direct light while the handle/waveguide assembly is secured to a dental drill, thereby providing illumination during drilling. Alternatively, the drill itself may be modified to include a fiber optic bundle in the drill cable and allow a disposable waveguide to be connected to this light source for drilling, then disposing of the waveguide after the procedure is finished.

Figure 3:
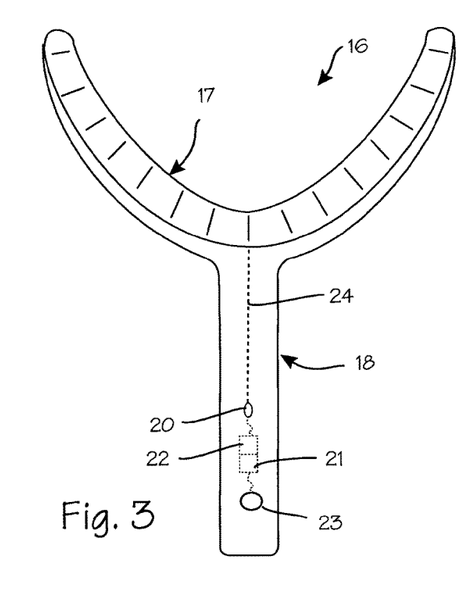
FIG. 3 is a top view of an alternate cavity illumination configuration as a dental retractor with a handle.

FIG. 3 illustrates a cavity illumination system for dental procedures using a dental retractor 16 with a U-portion 17 and a handle portion 18. The dental cavity illumination system comprises retractor 16 with an illumination source comprising an LED 20, battery 21, LED control 22 circuit, and switch 23 secured within handle 18. In this figure, the LED is mounted on the handle portion of the retractor and the illumination source further comprises an optical fiber 24 communicating from the LED to the U-shaped portion of the retractor. The U-shaped portion of the retractor acts as a waveguide and the optical output of the optical fiber travels through the U-shaped portion. The optical fiber is secured in a channel provided in the retractor. The handle portion of this retractor may serve as a heat sink for dissipating the heat generated by the LED, and additional heat sinks structures may be added. The handle portion assembly may also be manufactured and provided separately from the U-shaped portion of the retractor. This way, the U-shaped portion may be packaged separately from the handle portion to enable disposable use of the U-shaped portion with a non-disposable handle portion. The assembly may also be integrated into the retractor, and provided in sterile packaging in kits of retractors assembled to support dental procedures. Depending on the type of retractor, the waveguide may be designed to include channels for suction and irrigation, thereby providing an integrated dental device.

Figure 4:
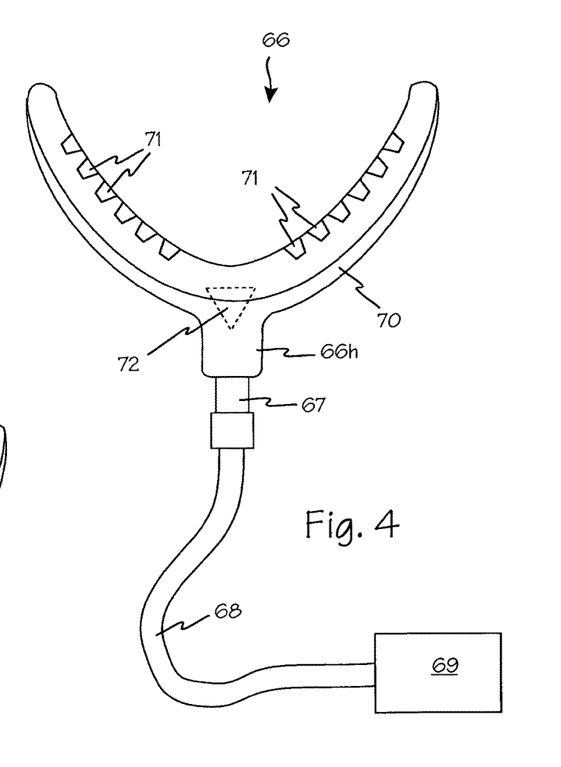
FIG. 4 is a top view of an alternate dental retractor cavity illuminator.

FIG. 4 shows a lip retractor waveguide 66 with a connector 67 at the handle end for connecting the waveguide to a fiber optic cable such as cable 68, which is connected to a suitable light source such as source 69. Handle portion 66h of the waveguide is designed and constructed to support total internal reflection of the light entering the waveguide from the fiber optic cable. Light travels down the handle where it spreads into U-shaped portion 70 and exits the waveguide through output optical structures 71 specifically designed to direct the light at particular locations, e.g., as spots or bands of light along the gum line or as a more diffuse light illuminating the gum line and teeth for a particular number of teeth or as a diffuse light illuminating the oral cavity, or some combination thereof.

Waveguide 66 may also include a light directing structure 72, in this case a prism that may be formed of a cutout or by insert molding a material of suitably different refractive index relative to the waveguide material, such structure serving to direct light toward the output optical structures located at the ends of the curved retracting portion to illuminate specific areas of the oral cavity.

Figure 5:
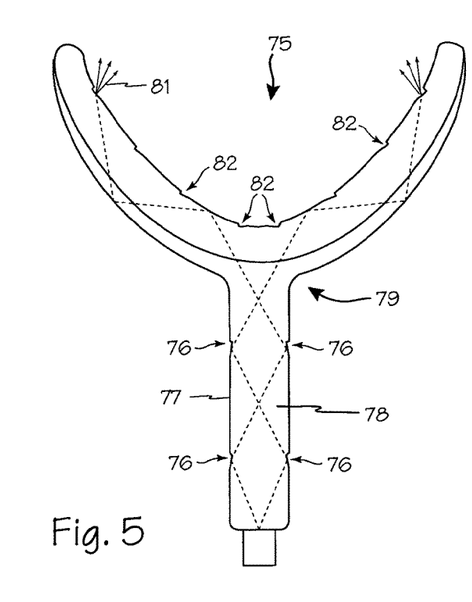
FIG. 5 is a top view of a dental retractor cavity illuminator with light directing structures.

Waveguide 75 of FIG. 5 includes light directing structures 76 on outer surface 77 of handle 78 or along the transition 79 of the handle to the U-shaped portion 80 or along the U-shaped portion that serve to efficiently direct the light into and along the U-shaped portion to maximize the amount of light 81 exiting the output optical structures 82 located along a substantial length of the curved retracting portion to illuminate a broad area while minimizing light loss in the waveguide.

Figure 6:
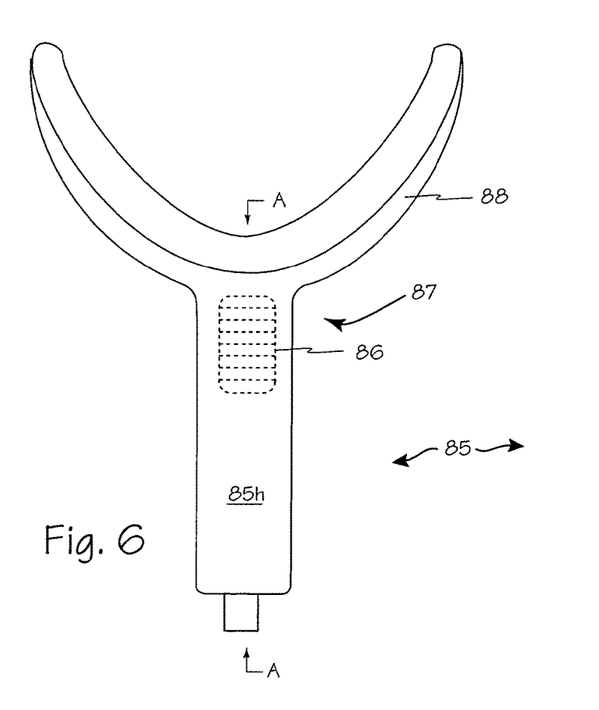
FIG. 6 is a top view of a dental retractor cavity illuminator with light directing structures in the handle.
Figure 7:
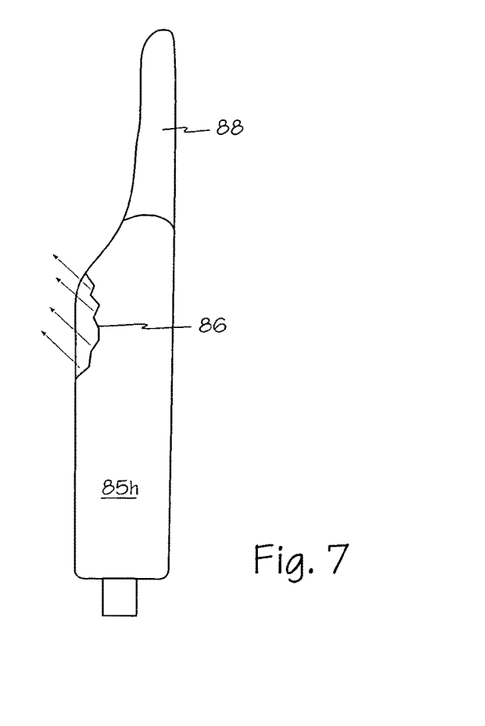
FIG. 7 is a cutaway view of the dental retractor cavity illuminator of FIG. 6.

Cavity illuminator 85 of FIGS. 6 and 7 includes output optical structures 86 located in handle portion 85h or the transition portion 87 between the handle and curved retracting portion 88. The location of output structures 86 as illustrated, serving to illuminate the front teeth, gums or other anatomical structures toward the front of the mouth. In an alternate configuration, optical output structures in the handle or transition portion may be combined with one or more light directing structure, e.g., a prism, and optical output structures along the curved retracting portion to direct light both at or from the front of the oral cavity as well as the sides of the oral cavity to illuminate oral anatomical structures for examination or treatment.

Figure 8:
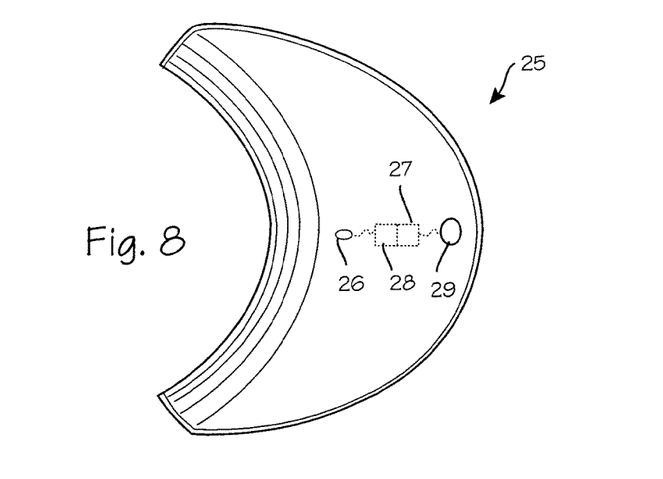
FIG. 8 is a top view of a cheek retractor cavity illuminator according to the present disclosure.

FIG. 8 illustrates a cavity illumination system using a cheek retractor. The cavity illumination system comprises a cheek retractor 25 manufactured from a biocompatible sterilizable polymer that is transparent or semi-transparent and acts as a waveguide. The retractor has an illumination source disposed therein. The illumination source comprises an LED 26 or other light source, a battery 27, a LED control circuit 28, and a switch 29. When in use, the light source in the cheek retractor provides an electromagnetic wave that propagates through the polymer resulting in the illumination of an oral cavity.

A cheek retractor cavity illuminator may also include a connector portion that allows connection to an external light source either directly or through a suitable light conduit, for example, a fiber optic cable. Light entering the connector portion may be propagated through the waveguide via total internal reflection to optical output structures located on a suitable surface. Light directing structures may be located on the external wall of the cheek retractor waveguide or within the body of the waveguide.

Figure 9:
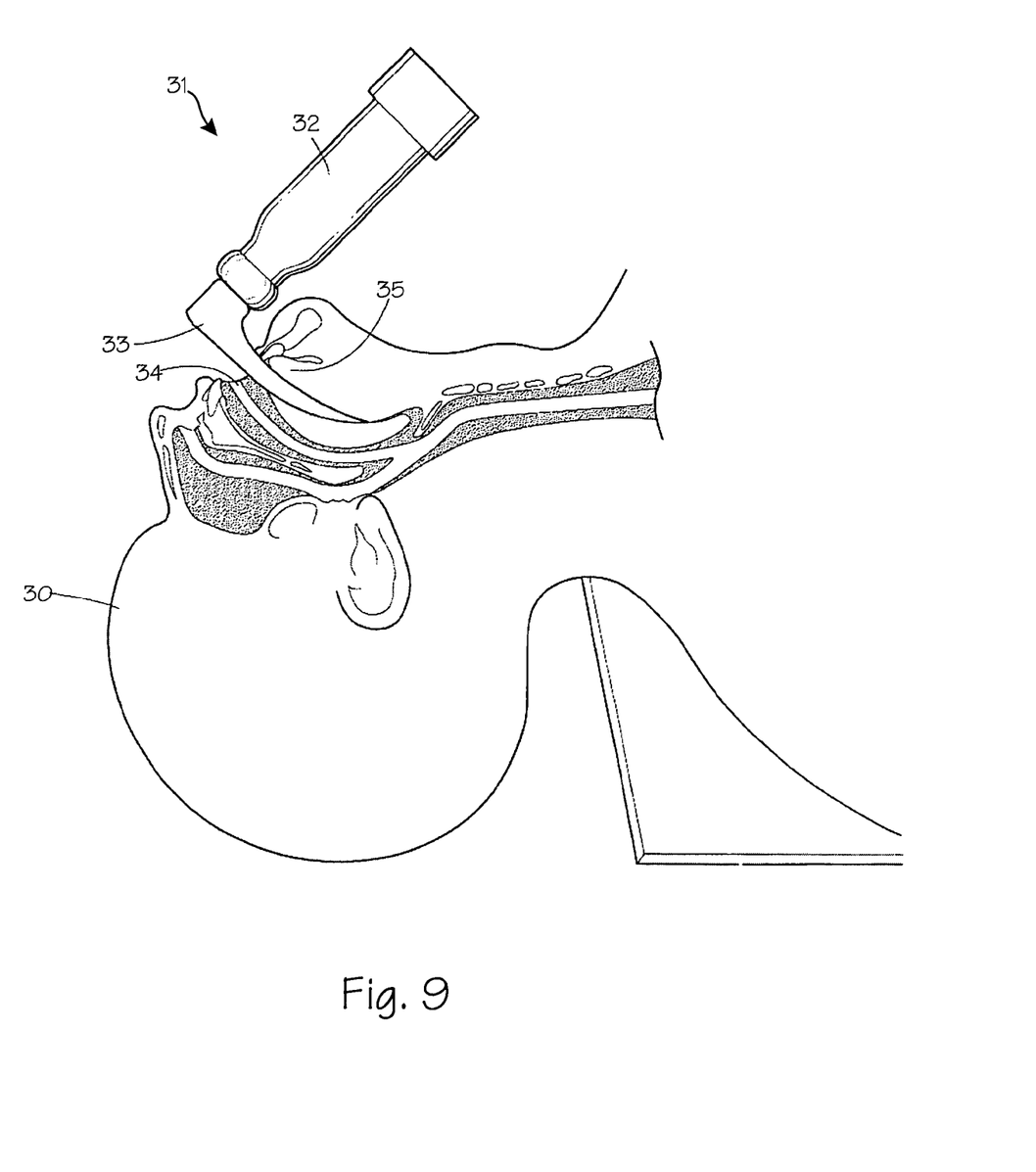
FIG. 9 is a side view of a laryngoscope cavity illuminator in use.

FIG. 9 illustrates a laryngoscope illumination system in use on a patient 30. The laryngoscope 31 includes a handle 32 and a blade 33. The handle 32 allows for grasping the laryngoscope 31. The blade 33 is rigid and is attached to and extending from the handle. The blade comprises biocompatible sterilizable polymer that acts as a waveguide and further comprises an illumination source. The blade is for inserting into the mouth 34 of a patient to allow viewing of a portion of the mouth, the pharynx, and the larynx of the patient 30. The blade is used to depress the tongue 35 and mandible in order to prevent the tongue 35 of the patient 30 from obstructing the view of the medical professional during examination. When the illumination source is illuminated, electromagnetic waves (light) are able to propagate through the blade and illuminate the mouth and trachea of the patient.

Figures 10, 11:
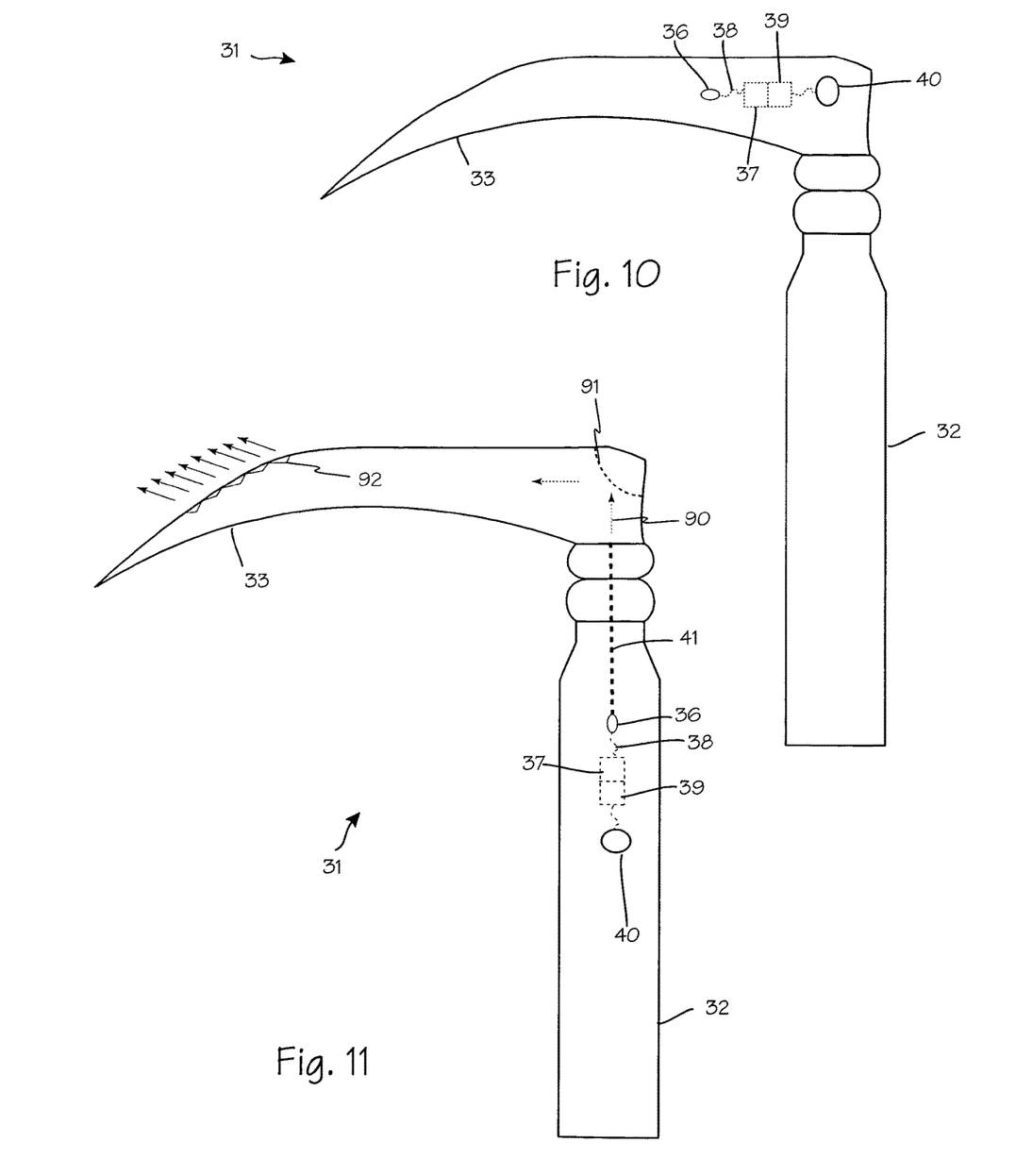
FIG. 10 illustrates a laryngoscope illumination system with an illumination source in the blade.
FIG. 11 illustrates a laryngoscope illumination system with an illumination source in the handle.

FIG. 10 illustrates the laryngoscope 31 of the laryngoscope illumination system in further detail. The laryngoscope 31 includes a handle 32 and a blade 33. The blade comprises a biocompatible sterilizable polymer that acts as a waveguide. The blade may have an illumination source disposed therein. The polymer may be transparent or semi-transparent. The illumination source disposed within the blade comprises one or more LEDS 36 (light emitting diodes), battery 37, a conductor 38 electrically connecting the battery and the LED, and an LED control circuit 39 and switch 40. The LED is preferably a white-light LED, which provides a bright, white light. The battery may be provided in any form, but is preferably a lithium ion polymer battery. The blade may also be detachable from the handle and disposable. The illumination source is in optical communication with the blade. When the illumination source is illuminated, light from the illumination source propagates through the blade illuminating the blade.

FIG. 11 illustrates an alternate laryngoscope illumination system with the illumination source in the handle of the laryngoscope 31. The laryngoscope 31 includes a handle 32 and a blade 33. The blade comprises a biocompatible sterilizable polymer that acts as a waveguide. The handle has an illumination source disposed therein. The polymer in the blade may be transparent or semi-transparent. The illumination source disposed within the handle comprises one or more LEDs 36 (light emitting diodes), battery 37, a conductor 38 electrically connecting the battery 37 and the LED 36, an LED control circuit 39, a switch 40 and an optical fiber 41 in optical communication between the LED 36 and the blade 33.

The light output 90 of the optical fiber travels to one or more light directing surfaces such as surface 91 where it is directed toward output optical structures 92 on any suitable surface of the blade. Output optical structures 92 may direct illumination to particular anatomical areas through refraction while minimizing reflection that contributes to loss of light. The LED is preferably a white-light LED, which provides a bright, white light. The battery may be provided in any form, but is preferably a lithium ion polymer battery. The optical fiber 41 is secured in a channel provided in the laryngoscope 31. LED 36 may be positioned in closer proximity to blade 33 such that light from LED 36 is captured directly by blade 33, perhaps using optical structures on the light input portion of blade 33 that efficiently capture light from LED 36, thereby obviating the need for optical fiber 41. The handle 32 of this laryngoscope may serve as a heat sink for dissipating the heat generated by the LED, and additional heat sinks structures may be added. The handle may also be manufactured and provided separately from the blade of the laryngoscope 31. This way, the blade 33 may be packaged separately from the handle to enable disposable use of the blade 33 with a non-disposable handle 32. When the illumination source is illuminated, light from the illumination source propagates through the optical fiber to the blade illuminating the blade 33. This in turn can illuminate the mouth and trachea of a patient.

Figures 12, 13, 14, 15:
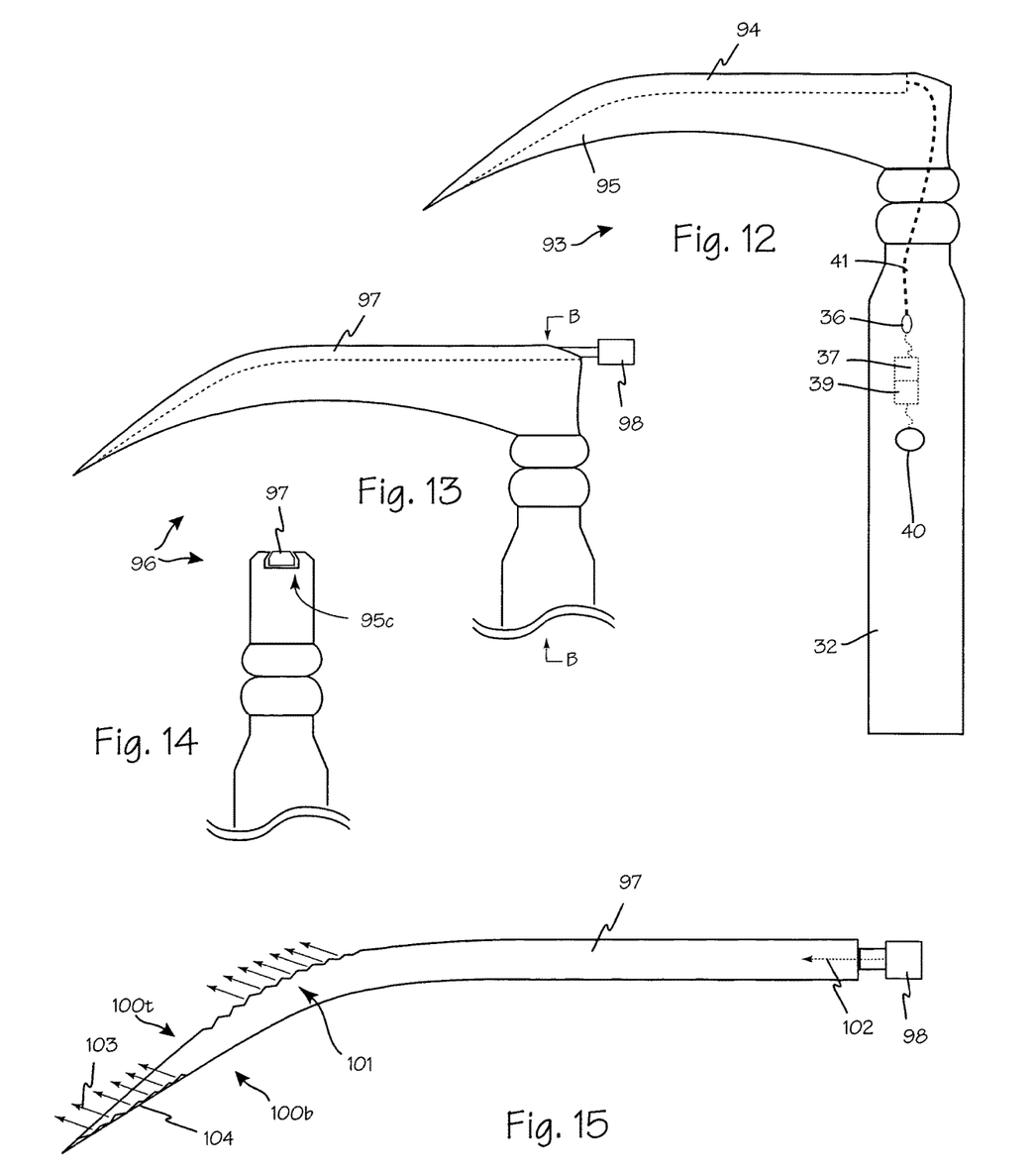
FIG. 12 is a side view of an alternate laryngoscope illuminator according to the present disclosure.
FIG. 13 is a side view of a metal blade laryngoscope including an illuminator waveguide engaging the blade.
FIG. 14 is a cutaway view of the laryngoscope cavity illuminator of FIG. 13 taken along B-B.
FIG. 15 is a side view of a laryngoscope cavity illuminator waveguide.

Cavity illuminator 93 of FIG. 12 includes a waveguide insert 94 attached to blade 95. The waveguide insert may be attached to the blade surface, e.g., with a suitable adhesive or other attachment means, or may be inserted into a channel formed in the blade to receive and hold the insert. The blade and handle may be separate pieces or integrated as a single device. In this embodiment, light from optical fiber 41 injects light into waveguide insert 94, said light traveling along the waveguide insert to exit at one or more optical output structures positioned at one or more designated areas of the waveguide insert. Optical fiber 41 may be replaced by any other suitable light conduit, such as a rigid or flexible light pipe or waveguide.

Referring now to FIGS. 13 and 14, cavity illumination system 96 including waveguide insert 97, the waveguide insert having an input connector 98 to couple light into the waveguide insert from an external light source, such as a fiber optic cable connected to xenon or tungsten light source as shown in FIG. 4. waveguide insert 97 may engage a channel 95c in the blade. The channel is designed to engage the insert. The waveguide insert may be made from a suitable hard plastic, such as polycarbonate or acrylic. The waveguide may also be made from a flexible optical material, such as silicone, and may be supplied with a stiffening member to make it easier to insert the flexible waveguide into the channel in the blade. The waveguide may be made to be single use disposable or made to be suitable for multiple uses. The light source contained in the blade injects light into the waveguide insert, said light then is contained in the waveguide and travels to output optical structures in the waveguide insert that direct light to particular anatomic areas.

Waveguide insert 97 as shown in FIG. 15 may include output optical structures such as structures 101 in one or more suitable locations to direct light to any appropriate anatomical areas. Output optical structures 101, here, stair stepped facets, running a portion of the length of the top surface of the waveguide insert, each of said facets causing a portion of the light 102 to exit the waveguide insert in a predetermined direction while minimizing light lost due to reflection at these structures in order to maintain high transmission efficiency. If the output optical structures abruptly end at an end face, light will shine out of this end face. However, the light that exits the end face may not serve as useful illumination and, hence, may be considered lost light that lessens the efficiency of the waveguide insert. To improve efficiency, one or more optical structures 104 may be arranged on bottom surface 100b of to direct light out of the corresponding top surface loot, which may have microstructured optical components to diffuse or further direct the light 103. Combining the bottom face output optical output structures 104 with the top face output optical structures 101 increases the transmission efficiency of the waveguide insert.

Figures 16, 17:
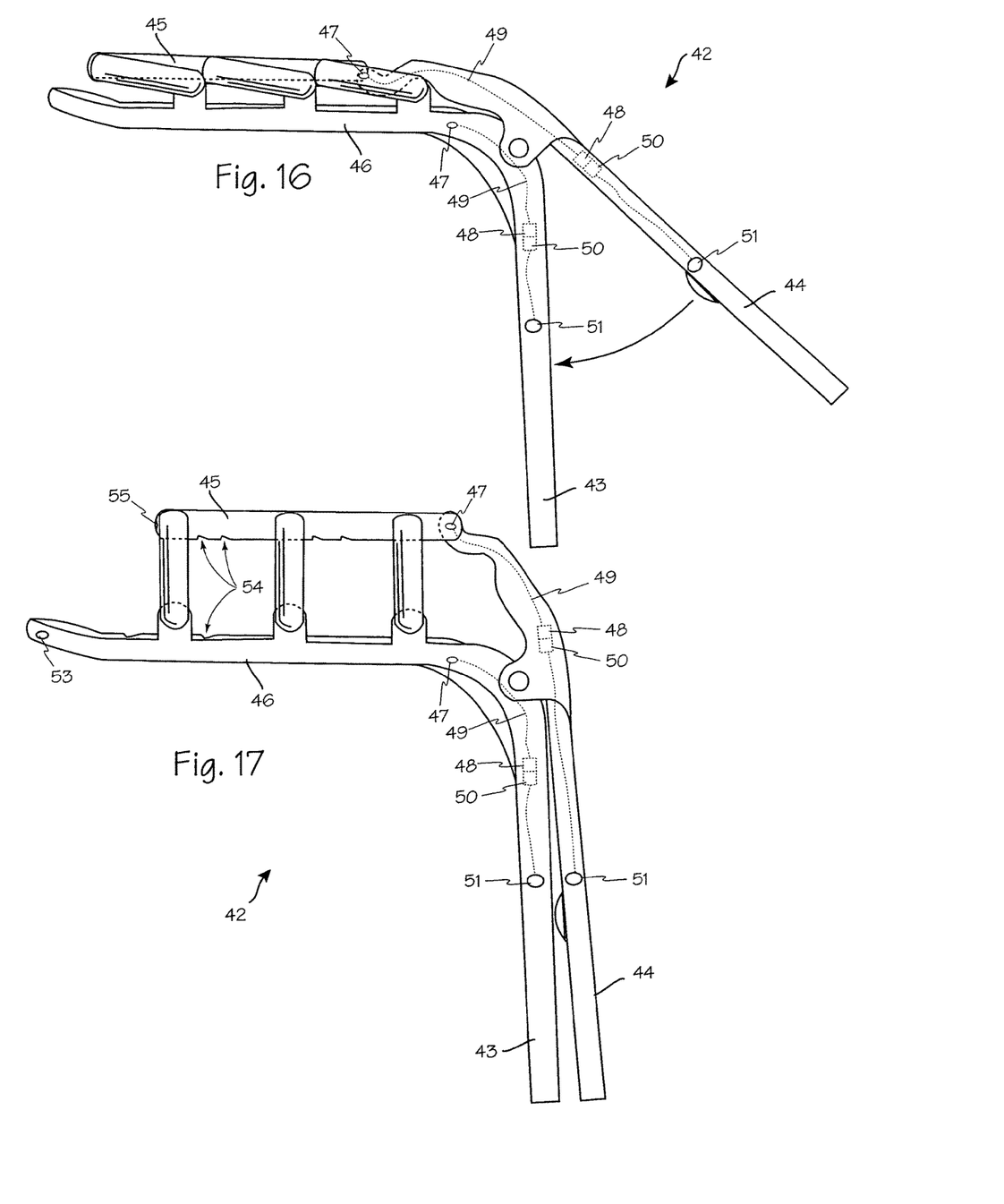
FIG. 16 illustrates the Speculum Illumination System.
FIG. 17 is a side view of the cavity illumination system of Figure with the handles closed.

FIG. 16 illustrates the speculum illumination system. Gynecological speculum 42 includes a first handle 43, a second handle 44, an upper blade 45 and lower blade 46. The upper blade 45 and lower blade 46 comprise a biocompatible sterilizable polymer that functions as a waveguide. The polymer may have holographic or complex prismatic properties and is designed to maximize light transmission efficiency to allow the use of lower power light sources. Each blade may engage an illumination source or have an illumination source disposed therein. The polymer may be transparent or semi-transparent. The illumination source disposed within the blades comprises one or more LEDs 47 (light emitting diodes), battery 48, a conductor 49 electrically connecting the battery and the LED, and an LED control circuit 50 and switch 51. The LED 47 is preferably a white-light LED, which provides a bright, white light. The battery may be provided in any form, but is preferably a lithium ion polymer battery. The blades may also be detachable from the handle and disposable. The illumination source is in optical communication with the respective blade. When the illumination source is illuminated, light from the illumination source propagates through the blade providing illumination from appropriate areas of the blade.

Referring now to FIG. 17, handles 43 and 44 are closed to separate blades 45 and 46. In this orientation, blades 45 and 46 may direct light into the cavity in which the device is engaged. Any suitable structure, or structures such as coating 53, facets 54 and or micro optical structures 55 may be incorporated into blades 45 and or 46 to control and direct illumination, however, such structure or structures must be specifically designed to maximize light transmission efficiency and minimize light loss and must be specifically designed to direct light to specific anatomic structures. For example, structures 54 may designed to direct more diffuse light to illuminate a substantial portion of the vaginal wall, or may be designed to direct more focused light to illuminate the cervix at the end of the vaginal cavity, or may be designed to provide both types of illumination. Single or multiple refractive and/or reflective structures, which may be combined with microstructured optical components, may be used to maximize light transmission efficiency to allow lower power light sources to be used, thereby reducing heat generation and the need to provide cumbersome heat management devices and methods.

Figure 18:
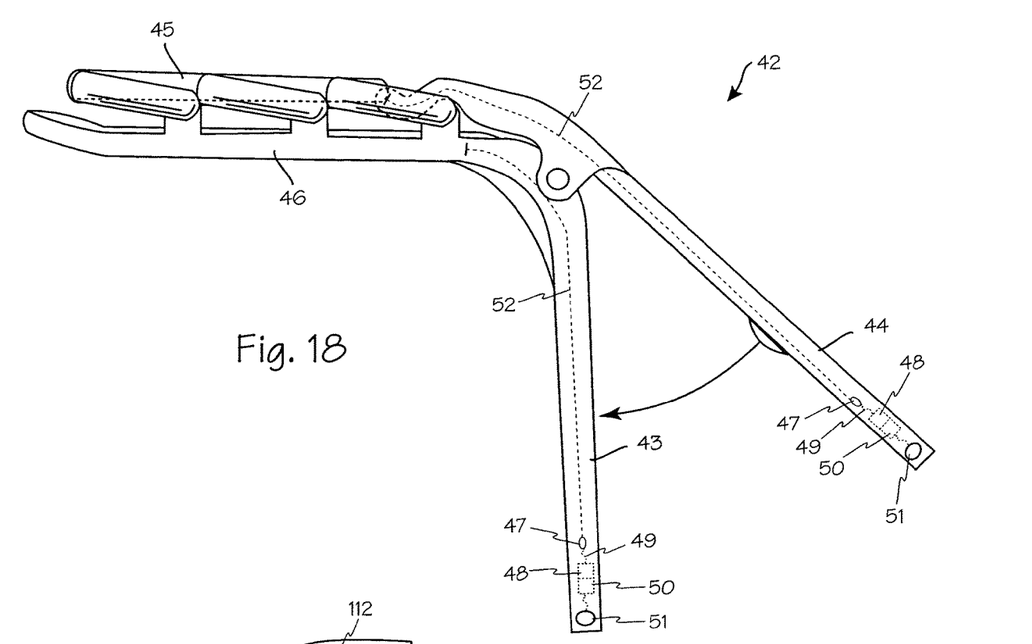
FIG. 18 is a side view of an alternate cavity illumination system with the illumination source in the handle.

FIG. 18 illustrates an alternate cavity illumination system with the illumination source in the handles 43 and 44 of the speculum 42. The speculum 42 includes a first handle 43, a second handle 44, an upper blade 45 and lower blade 46. The blades 45 and 46 comprise a biocompatible sterilizable polymer that functions as a waveguide. The polymer may have holographic or complex prismatic properties and is designed to maximize light transmission efficiency to allow the use of lower power light sources. The handles have an illumination source disposed therein. The polymer in the blade may be transparent or semi-transparent. The illumination source disposed within one or both handles comprises one or more LEDs 47 (light emitting diodes), battery 48, a conductor 49 electrically connecting the battery and the LED, an LED control circuit 50, a switch 51 and an optical fiber 52 in optical communication with the LED and a blade. The optical output of the optical fiber 52 travels through the blade illuminating the anatomical area(s) of interest. The LED is preferably a white-light LED, which provides a bright, white light. The battery may be provided in any form, but is preferably a lithium ion polymer battery. The optical fiber is secured in a channel provided in the speculum. The handles of this speculum may serve as a heat sink for dissipating the heat generated by the LED, and additional heat sinks structures may be added. The handles may also be manufactured and provided separately from the blades of the speculum. This way, the blades may be packaged separately from the handle to enable disposable use of the blade with a non-disposable handle. When the illumination source is illuminated, light from the illumination source propagates through the optical fiber to the blades illuminating the upper blade and lower blade. This in turn can illuminate the vaginal cavity a patient.

Speculums with metal blades continue to be used. If a metal speculum is preferred, then a disposable waveguide insert, similar to that shown in FIG. 19 or FIG. 20, may be provided.

Figures 19, 19A, 19B:
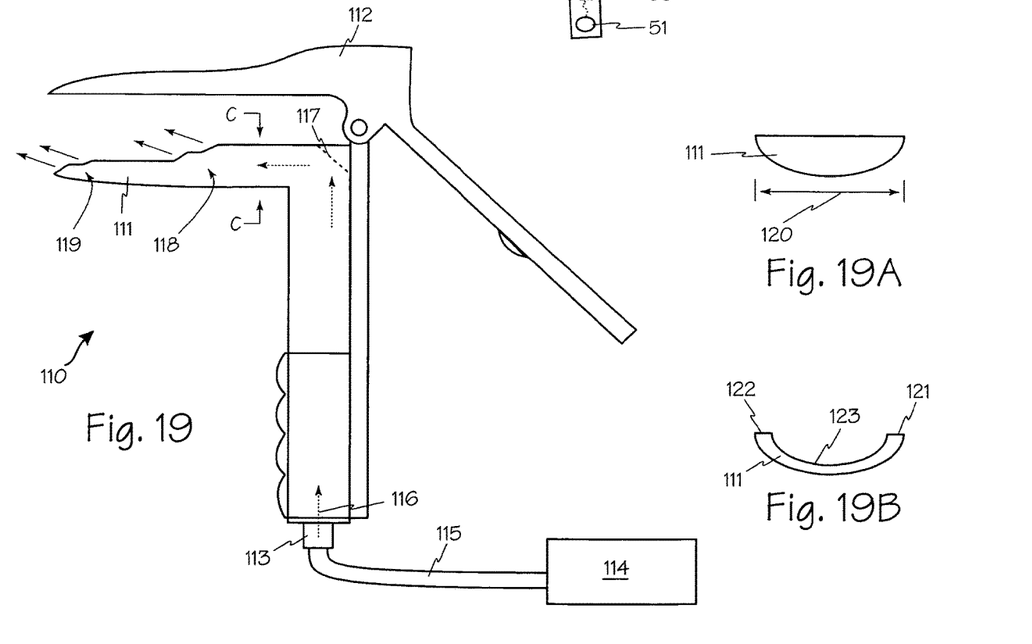
FIG. 19 is a side view of another alternate cavity illumination system.
FIG. 19A is a cutaway view of the blade of cavity illumination system of FIG. 19 taken along C-C.
FIG. 19B is a cutaway view of an alternate blade of cavity illumination system of FIG. 19 taken along C-C.

Speculum 110 of FIG. 19 may be a disposable speculum comprised of an illuminating bottom blade 111 (waveguide blade) and a non-illuminating top blade 112. Waveguide blade 110 has an input connector 113 for a suitable light source, such as a fiber optic cable 115 connected to an external xenon light source 114. Light 116 enters the connector portion of the waveguide blade and travels up the handle portion to a light directing structure 117, which directs the light 90 degrees toward the output optical structures 118 and 119 located along the bottom blade portion.

If bottom blade 111 has a solid cross-section as shown in FIG. 19A, output optical structures such as structures 118 and 119 may extend the full width 120 of blade 111 as well. If the bottom blade has a cup-shaped cross-section as shown in FIG. 19B, separate output optical structures may be located on edge faces 121 and 122 as well as on concave surface 123. The output optical structures direct light to specific anatomic areas and such light may be more diffuse, more focused, or a combination of each. The waveguide blade may be fabricated with suitable waveguide material as an optical element co-molded or over-molded with a suitable non-optical material as a structural element. The waveguide blade is normally designed to maximize light transmission efficiency.

Figure 20:
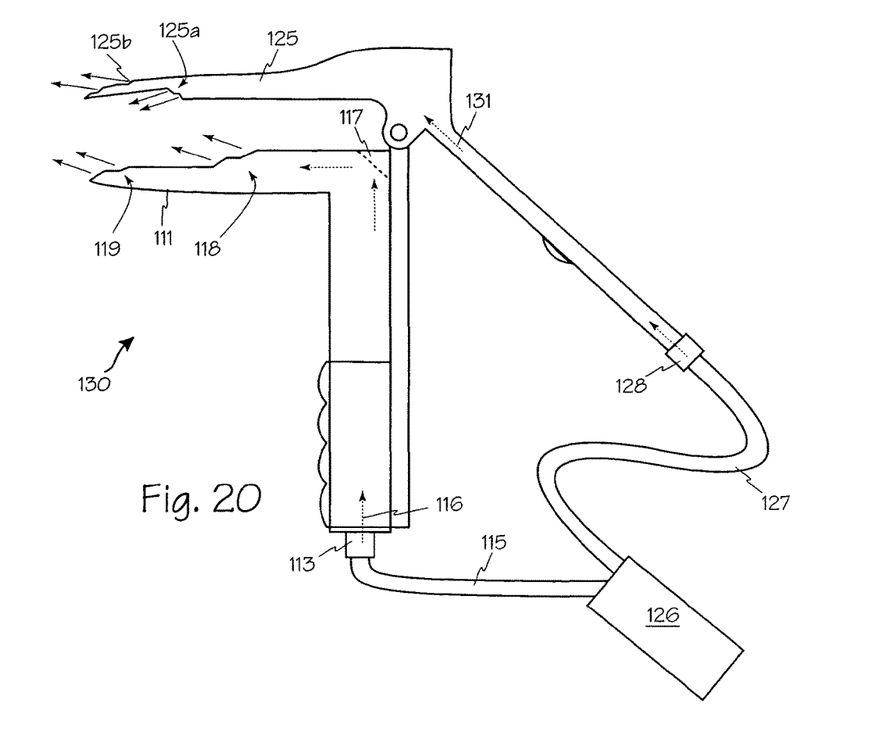
FIG. 20 is a side view of still another alternate cavity illumination system.

Cavity illumination system 130 of FIG. 20 may include two waveguide blades, 111 and 125. The bottom waveguide 111 is as described for FIG. 19. Top waveguide blade 125 may include a connector 128 for a separate light source or both the top and bottom waveguide blades may be connected to the same light source 126. Top waveguide blade 125 may not need internal light directing structures, such as structure 117 in blade 111, because its normal geometry may provide suitable reflecting surfaces for directing light 131 toward the output optical structures 125a and 125b. Top waveguide blade may have a similar output optical structure as the bottom waveguide blade. Together, the two blades provide even illumination of the entire cavity wall. Each waveguide blade may be designed to maximize light transmission efficiency. Alternatively, each blade may have different output optical characteristics to provide complimentary illumination, each blade illuminating different areas or anatomy.

Figure 21:
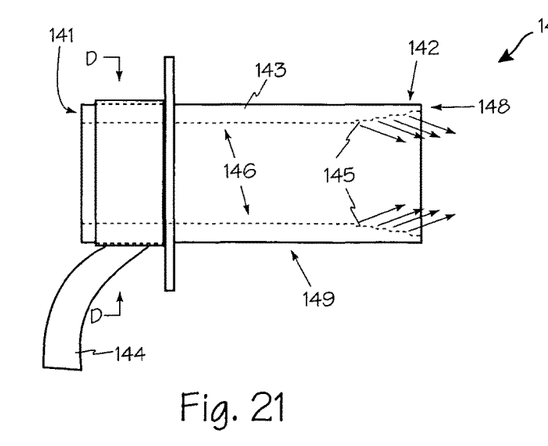
FIG. 21 is a top view of yet another cavity illumination system according to the present disclosure.

FIG. 21 illustrates a side view of an illuminating anoscope waveguide 140 with a proximal end 141 and a distal end 142 that is inserted into a patient's natural cavity such as the anal cavity. The anoscope waveguide 143 may also be used as a general speculum. The anoscope waveguide is normally molded from a suitable optical material, such as polycarbonate or acrylic. It may also include an input connector 144 that serves to conduct light into the waveguide such that light is conducted around the entire circumference of the waveguide tube. Output optical structures 145 are typically placed near the distal end on the inside wall 146 along all or a portion of circumference 147. Output optical structures placed on the end face 148 or outside wall 149 might cause irritation to the cavity walls during insertion. If output optical structures are required on end face 148 or outside wall 149, any suitable coating or material may be used to lessen the irritation. The output optical structures provide even illumination of the entire cavity wall. The waveguide is designed to maximize light transmission efficiency. For example, a reflective or prismatic surface may be created on the proximal end face to send mis-reflected light rays back toward the distal output optical structures.

Figure 22:
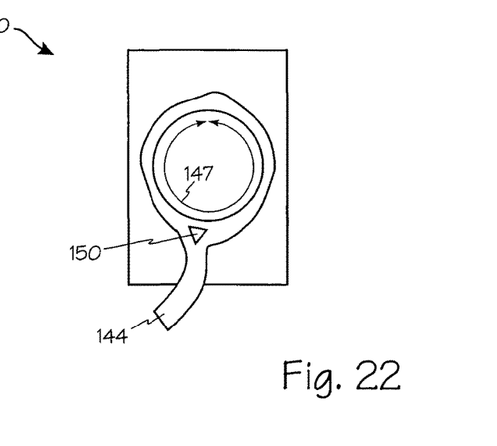
FIG. 22 is a cutaway view of the cavity illumination system of FIG. 21 taken along D-D.

Referring now to FIG. 22 shows an example of a light directing structure that contributes to light distribution around circumference 147. Light entering input connector 144 may be directed by a light control structure, such as structure 150, which splits the incoming light and sends it down into the waveguide tube wall at an angle ensuring circumferential light distribution.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A tubular retractor comprising:
   a tubular wall configured to be inserted in a body cavity, and wherein the tubular retractor is a waveguide;
   an input connector configured to receive light from an illumination source and transmit the light into the tubular retractor; and
   a plurality of output optical structures disposed on the tubular wall,
   wherein the output optical structures are configured to direct the light from the illumination source to the body cavity, and
   wherein the plurality of output optical structures comprise a plurality of stair stepped facets.

2. The tubular retractor of claim 1, wherein the plurality of stair stepped facets comprise at least three stairs on the tubular wall of the tubular retractor.

3. The tubular retractor of claim 2, wherein the at least three stairs are arranged in a sequence along a longitudinal axis of the tubular wall and wherein each stair has a distal surface which is formed at a non-parallel angle relative to the longitudinal axis.

4. The tubular retractor of claim 1, wherein the waveguide is formed from at least one optical material selected from a group consisting of: polycarbonate, acrylic, or silicon.

5. The tubular retractor of claim 4, wherein the waveguide is configured to propagate light from the input connector at a proximal end of the tubular wall toward a distal end of the tubular wall.

6. The tubular retractor of claim 5, wherein the plurality of output optical structures are disposed adjacent to the distal end of the tubular retractor.

7. The tubular retractor of claim 6, further comprising a light directing surface adjacent to the input connector, the light directing surface configured to distribute light around a circumference of the tubular wall and from the input connector toward the plurality of output optical structures.

8. The tubular retractor of claim 6, wherein a reflective or prismatic surface is adjacent the proximal end of the tubular retractor, the reflective or prismatic surface configured to direct mis-reflected light back toward the plurality of output optical structures.

9. The tubular retractor of claim 1, wherein the tubular retractor forms a cylinder.

10. The tubular retractor of claim 1, wherein the plurality of output optical structures are disposed on an inside wall of the tubular retractor.

11. The tubular retractor of claim 1, wherein the plurality of output optical structures are disposed on an outer wall of the tubular retractor.

12. The tubular retractor of claim 1, wherein the plurality of output optical structures are disposed on an end face of the tubular retractor.

13. The tubular retractor of claim 1, wherein a coating is disposed on the plurality of output optical structures, wherein the coating is at least one of a group consisting of: a reflective coating and a dampening coating.

* * * * *